United States Patent [19]

Mittelman et al.

[11] Patent Number: 4,583,554
[45] Date of Patent: Apr. 22, 1986

[54] KNEE LIGAMENT TESTING DEVICE

[75] Inventors: Jonathan S. Mittelman, Albuquerque; John S. Romine, Farmington, both of N. Mex.

[73] Assignee: Medpar II, Albuquerque, N. Mex.

[21] Appl. No.: 619,799

[22] Filed: Jun. 12, 1984

[51] Int. Cl.⁴ .............................................. A61B 6/00
[52] U.S. Cl. .................................. 128/774; 128/782; 73/789
[58] Field of Search ............... 128/774, 779, 781, 782; 73/789, 849, 852–854, 856; 33/174 D

[56] References Cited

U.S. PATENT DOCUMENTS

| 4,037,480 | 7/1976 | Wagner | 128/782 |
| 4,306,571 | 12/1981 | McLeod, Jr. | 128/782 |
| 4,323,080 | 4/1982 | Melhart | 128/774 |

OTHER PUBLICATIONS

Research Disclosure, "Wrist and Shoulder Motion Analyzer", 11/81.
Long et al., "Knee Analyzer . . . ", Med. Biol. Eng. & Comput., 9/77.
D. Daniel, M.D., et al, "Instrumented Measurement of Acute ACL Disruption", Departments of Orthopedic Surgery, Kaiser Hospital and University of California at San Diego (1984).
"Knee Laxity Tester", by Stryker Corporation, Kalamazoo, Michigan (1983).

Primary Examiner—Edward M. Coven
Attorney, Agent, or Firm—Richards, Harris, Medlock & Andrews

[57] ABSTRACT

A knee ligament testing device (10) is disclosed for use in testing the ACL ligament of the knee. The device includes a force application arm (12) and reference arm (18) which are hinged at a pivot joint (20). A predetermined maximum force can be applied to the force application arm (12) by exerting force on a torque limiter (26) inserted in an aperture (38) in the force application arm (12). The torque limiter (26) insures that the identical force will be applied on a leg for every test to insure reproducibility and prevents the application of excessive force to the leg. Displacement of the tibia relative to the femur is sensed by movement of an inner tube (56) relative to an outer tube (54) which is translated into rotational movement of an input shaft through potentiometer (66). The change in resistance in the potentiometer (66) is analyzed and converted to a linear measurement which is displayed on a display (72).

10 Claims, 6 Drawing Figures ized examination can diagnose internal knee derangement and provide the basis for a well informed decision to perform surgey to repair the structure. However, an arthroscopic examination of the knee costs approximately $2,000 and does entail some risk of harm. Therefore, there is a need to find a less costly and equally effective technique of diagnosing injuries to the internal structure of the knee.

KNEE LIGAMENT TESTING DEVICE

TECHNICAL FIELD

This invention relates to an apparatus and method for quantitatively measuring the disruption of the anterior cruciate ligament of the knee.

BACKGROUND OF THE INVENTION

In the course of a normal day, the knee joint of an active individual is the one anatomical structure most stressed, and therefore, most prone to injury. While physical examination can determine the extent of most injuries, at the present time only a surgical arthroscopic examination can diagnose internal knee derangement and provide the basis for a well informed decision to perform surgey to repair the structure. However, an arthroscopic examination of the knee costs approximately $2,000 and does entail some risk of harm. Therefore, there is a need to find a less costly and equally effective technique of diagnosing injuries to the internal structure of the knee.

A knee joint is composed of both internal and external components. The internal components include the articular cartilages, or menisci, and the cruciate ligaments (both anterior and osterior.) The external components include the capsule and collateral ligaments. The knee joint operates to provide a force transmitting articulation between the upper leg bone (the femur), and the lower leg bone (the tibia). The knee cap, or patella, rests generally on the femur and is enclosed by the patellar tendon.

The integrity of the knee joint is maintained by the ligaments. The cruciate and the collateral ligaments are particularly important in this function. Of these ligaments, the cruciate ligaments are considered by far the most complex structure in the knee joint. The anterior and posterior cruciate ligaments cross each other at the center of the knee joint, and each is attached to both the femur and the tibia.

Any anterior or posterior movement of the proximal (or upper) end of the tibia relative to the distal (or lower) end of the femur is resisted by the tensile forces developed in the cruciates. Thus, forward (or anterior) movement of the tibia relative to the femur will result in increased tension in the anterior cruciate ligament.

Classically, injury to the anterior cruciate ligament (ACL) is caused by a deceleration twisting injury of the knee. This is associated with a "pop" from deep within the knee, an inability to continue any activity using the knee, and the development within 24-hours of a tense infusion (swelling) of the knee. If the syndrome is properly identified, diagnosis of ACL injury will be correct 90% of the time, with repair possible in 77% of the cases. For repair to be possible, it must be carried out within ten (10) days of the injury. However, these figures do not reflect how many cases of ACL injury go undiagnosed, leading to chronic knee instability in many cases.

Experiments conducted by the Department of Orthopedic Surgery at Kaiser Hospital and the University of California, both in San Diego, have demonstrated that the forward displacement of the tibia relative to the femur upon application of a force to the calf of the lower leg results in a displacement of the tibia relative to the femur in the anterior/posterior plane. The amount of displacement for a given force varies widely in the normal population. However, if it has been found that in the normal population there is less than a 2 millimeter displacement difference between displacement measured on the legs of a given individual for a given force, usually 20 pounds. If the difference in displacement between the legs of the individual is in the range of 2.0 to 2.5 millimeters, ACL disruption in the leg showing the largest displacement is suggested. If a 3 millimeter displcement difference exists between the legs of the individual, a diagnoses of ACL disruption is indicated. A summary of the studies is found in a paper prepared for the annual meeting of the American Association of Orthopedic Surgeons presented in Atlanta, Georgia in 1984.

Several techniques have been used in the past for applying forces to the legs of an individual to diagnose ACL injury manually. Neither of these manual tests are sensitive enough to accurately and reproducibly measure the difference in displacement between the legs of an individual. The anterior drawer test is performed with the knee flexed to 90° and the foot stabilized. The examiner puts both hands around the upper end of the lower leg and draws the tibia toward himself to determine displacement. However, muxcular spasms of tense joint effusion can occasionally cause a false-negative anterior drawer sign. Therefore, the so-called Lachman's test, performed in a similar manner to the drawer test, but at 20° of flexion is considered a more sensitive test.

At least one device has been suggested for performing the Lachman test with sufficient accuracy to measure the difference in displacement between the legs of an individual. This device is identified as a knee laxity tester and is manufactured by the Stryker Corporation of 420 Alcottstreet, Kalamazoo, Mich. However, a fully satisfactory device for quantitatively and reproducibly measuring lasity of the anterior cruciate ligament of the knee has not yet been developed. The device should combine safety for the individual tested with ahigh accuracy and reproducibility of test results.

SUMMARY OF THE INVENTION

In accordance with one aspect of the present invention, an apparatus is provided for measuring the relative displacement of thetibia and femur upon application of a force by an operator. The apparatus includes a force application arm defining a rigid surface for contacting the lower leg for application of a force on the tibia. A reference armis pivotally hinged to the force application arm and also defines a rigid surface for contacting the upper leg for application of a force on the femur to counter the force applied to the tibia. Structure is provided which includes a handle for grasping by the operator to apply a force on the tibia through the force application arm with the operator simultaneously applying a counter force on the reference arm. The structure limits the force applied to the tibia to a predetermined maximum force to provide reproducibility of the displacement measurement and to prevent application of excessive force. A displacement sensor is mounted on the reference arm and has a tube mounted for movement relative to the reference arm along an axis generally parallel the direction of the force applied to the femur. One end of the tube contacts the lower leg in a fixed relation with the tibia at the level of the tibial tubercle. Finally, a measuring device is provided for measuring the displacement between the reference arm and the tube when the force is applied which corresponds to the displacement between the femur and the tibia.

In accordance with another aspect of the present invention, the measurement device includes a rotary linear potentiometer and a mechanism for converting the linear displacement of the tube to rotary movement of the potentiometer for measuring the displacement to an accuracy of approximately 0.1 millimeters.

In accordance with another aspect of the present invention, electronic circuitry is provided for measuring the resistance of the rotary linear potentiometer and generating an output signal to indicate the displacement. The electronic circuitry nulls the response to the potentiometer before applicationof force and holds the peak value of displacement after application of the force.

BRIEF DESCRIPTION OF THE DRAWINGS

For a more complete understanding of the present invention, reference is now made to the following Detailed Description, taken in conjunction with the accompanying drawings in which.

DETAILED DESCRIPTION

Figure 1:
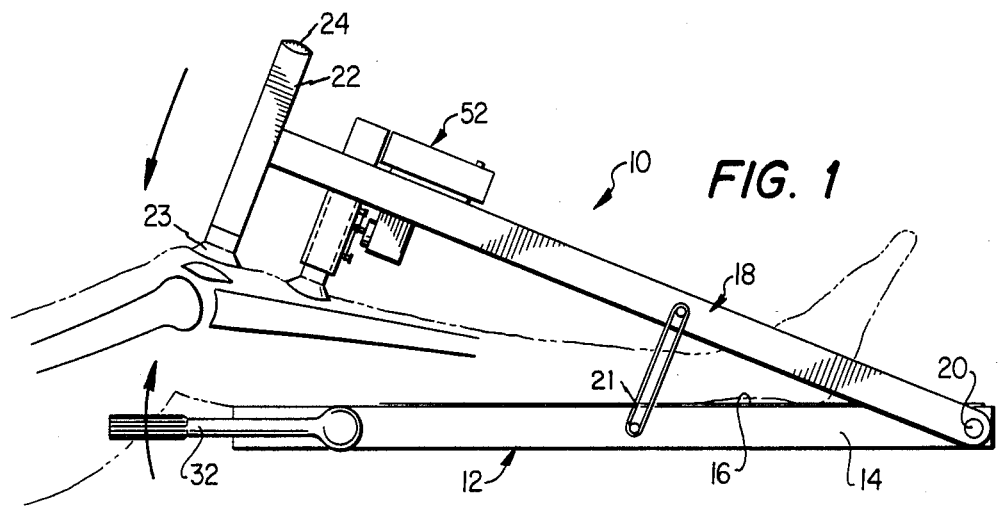
FIG. 1 is a side view of a testing device constructed in accordance with the techings of the present invention illustrating how the device is used with the leg.
Figure 2:
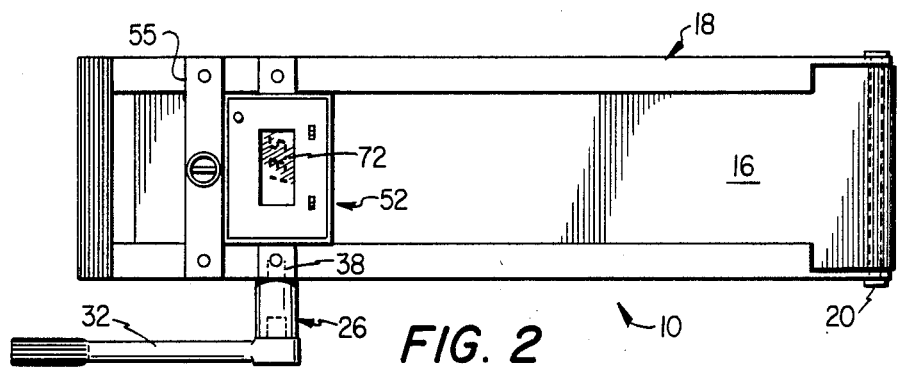
FIG. 2 is a top view of the testing device illustrating the LCD display of the tibia displacement.

FIGS. 1 and 2 illustrate a knee ligament testing device 10 which is specifically adapted to safely and accurately indicate the condition of the ACL ligament. The device 10 is designed to limit the force that can be exerted against the leg, thereby minimizing the risk of injury and discomfort to the patient. In addition, the device is designed to detect displacement between the tibia and femur to an accuracy of 0.1 millimeters and to provide a high standard of reproducibility of test results.

With reference now to the specific details of the device 10, the device 10 includes a force application arm 12. The force application arm includes a rigid frame 14 and a rigid support surface 16 on top of frame 14 for supporting the lower leg of the patient at the calf muscles, as seen in FIG. 1. In use, the patient's knee is flexed approximately 20° by a roll placed under the popliteal fossa. This relaxes the lateral and medial collateral ligaments and allows the cruciate ligaments to absorb whatever force is applied to the knee.

A reference arm 18 is also provided which is pivotally attached to the force application arm 12 by a pivot joint 20. The pivot joint is positioned below the location of the patient's ankle during use. As can be readily seen, the reference arm 18 is limited by the pivot joint 20 to motion in a plane which corresponds to the anterior/posterior plane of motion of the knee when the leg is positioned within the device as seen in FIG. 1. This anterior/posterior plane of motion of the knee is a plane parallel to the sagittal plane through the midpoint of the knee. An elastic band 21 extends between arms 12 and 18 to hold the device 10 in position on the lower leg.

A support 22 is rigidly secured at the end of the reference arm 18 opposite the pivot joint 20. One end of the support 22 has a pad 23 for contacting the patella or knee cap of the patient. If the patella is missing, the pad 23 can contact the femur directly. The opposite end of the support 22 is provided with a hand grip 24 for grasping by the person conducting the test to counteract the force applied to the leg by the force application arm 12 as discussed hereinafter. Because the patella is essentially resting on the lower end of the femur bone, the reference arm 18 is supported in a fixed relation with the lower end of the femur through the support 22.

Figure 5:
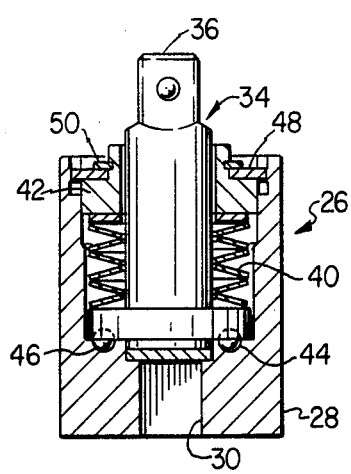
FIG. 5 is a cross-sectional view of the torque limiter.

In use, the operator applies a force to the calf portion of the lower leg by lifting up on the force application arm 12 while counteracting the force by supporting the femur through the reference arm 18 at the hand grip 24. To provide a limit on the force application, and permit application of consistent forces to provide for reproducibility of the test results, the force applied to the force application arm 12 is applied through a torque limiter 26 as seen in FIGS. 2 and 5. The torque limiter 26 is preferably of the type sold as model 12A1 by the X-4 Corporatin, 444 Chelmsford Road, North Billerica, Mass. 01862. The torque limiter 26 includes a body 28 which has a square aperture 30 for receiving the square drive potion of a conventional socket wrench 32 as seen in FIGS. 1 and 2. An output stub 34 is positioned within a recess in the body 28 and is provided with a square drive 36 which will be received by a square cross-section aperture 38 in frame 14 of the force application arm 12. The output stub 34 is designed to permit rotation relative to the body 28 against a predetermined and constant frictional resistance, which provides the torque limitation between the input to the body 28 and the output from output stub 34. The frictinal force is developed by a series of springs 40 acting between an adjustment nut 42 threaded to the body 28 and a portion of the output stub 34. The force from springs 40 urge a friction surface 44 on the output stub 34 against a friction surface 46 on the body 28. The force of the springs 40 can be adjusted by rotating the adjustment nut 42. Once adjusted, the adjustment nut 42 can be maintained stationary by a locking plate 48 and snap ring 50. As long as the torque applied to the body does not exceed the frictional forces between the body and output stub, the output stub will rotate with the body. However, when a predetermiend torque is achieved, the frictional forces between the body 28 and output stub 34 will be overcome and the output stub 34 will begin to slip relative to the body. Regardless of how much torque is applied to the body 28, the torque at the square drive 36 of the output stub 34 will never exceed the set predetermined maximum torque.

As can be seen in FIGS. 1 and 2, the torque limiter 26 can be employed to provide a predetermined and limited force on the lower leg through the force application arm 12. The torque limiter 26 is mounted with the square drive 36 in the aperture 38 of the arm 12. The socket wrench 32 is then positioned generally perpendicular to the direction of force application and is lifted upward to apply force to the lower leg. The force is limited by the torque limiter 26 to the desired level. Preferably, the force applied to the lower leg through the force application arm 12 will be approximately 20 pounds. However, the force can be varied by the operator depending on the patient.

Figure 4:
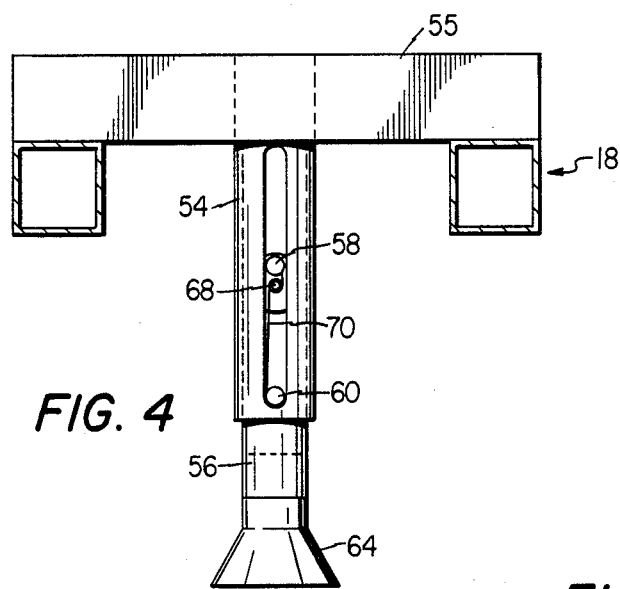
FIG. 4 is a vertical cross-section of a portion of the reference arm illustrating the displacement measuring components.
Figure 3:
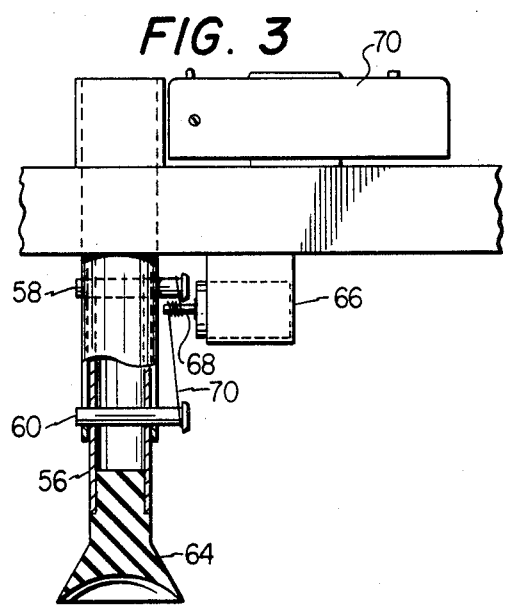
FIG. 3 is a partial side view of the testing device illustrating details of the displacement measuring components of the device.

Once the force is applied, the actual displacement of the tibia relative to femur is measured by a transducer module 52 that is secured on the reference arm 18 generally above the tibial tubercle in the lower leg. As seen in FIGS. 1, 3 and 4, the module 52 includes a fixed outer tube 54 which is secured to a cross piece 55 of the reference arm 18 along the center line thereof and extends generally in a direction parallel thatof the forces applied to the leg and parallel the direction of displacement of the tibia. The outer tube 54 has elongate slots in opposite sides which extend generally along the direction of displacement. A movable inner tube 56 fits within the outer tube 54 and is permitted to move along the direction of displacement. Two posts, 58 and 60, extend through two sides of the inner tube 56, and through the slots formed in the outer tube 54. The posts restrict sideways movement of the inner tube 56 relative to outer tube 54 and insure that the inner tube moves only in the anterior/posterior plane of the leg. A pad 64 is secured at the lower end of the inner tube 56 for contact with the top of the lower leg near the tibial tubercle. As force is applied to the leg through the force applicator arm 12, the reference arm 18 and femur remain stationary because the operator will prevent motion by counteracting the force through thehand grip 24 on the reference arm 18. However, the tibia will move in the anterior/posterior plane relative to the femur and this displacement will be duplicated by a displacement of the inner tube 56 relative to the outer tube 54.

The displacement of the tibia from the femur can be measured by the movement of the inner tube 56 relative to the outer tube 54 by use of a multiturn linear potentiometer 66 rigidly mounted on the reference arm 18 as seen in FIG. 3. The potentiometer 66 has an input shaft 68 which varies the resistance of the potentiometer 66 when rotated. A string 70 is secured at its ends to the posts 58 and 60 and wrapped several times around the input shaft 68 as seen in FIG. 3. Therefore, any movement of the inner tube 56 relative to the outer tube 54 and the remainder of the reference arm 18 will translate into rotational movement of the input shaft 68. Rotation of the input shaft 68 will, in turn, vary the resistance of the potentiometer 66 to a degree directly related to the displacement of the inner tube 56 relative to the outer tube 54. In one testing device constructed in accordance with the teachings of the invention, the posts 58 and 60 are positioned 1.5 inches apart and the slots 62 are 3 inches long. The potentiometer 66 is a 10 Kohm linear potentiometer. The string is formed by a braided, nonelastic nylon cord with four turns taken around the input shaft 68 to reduce slippage. In addition, the cord is permanently affixed to the shaft at its midpoint.

Figure 6:
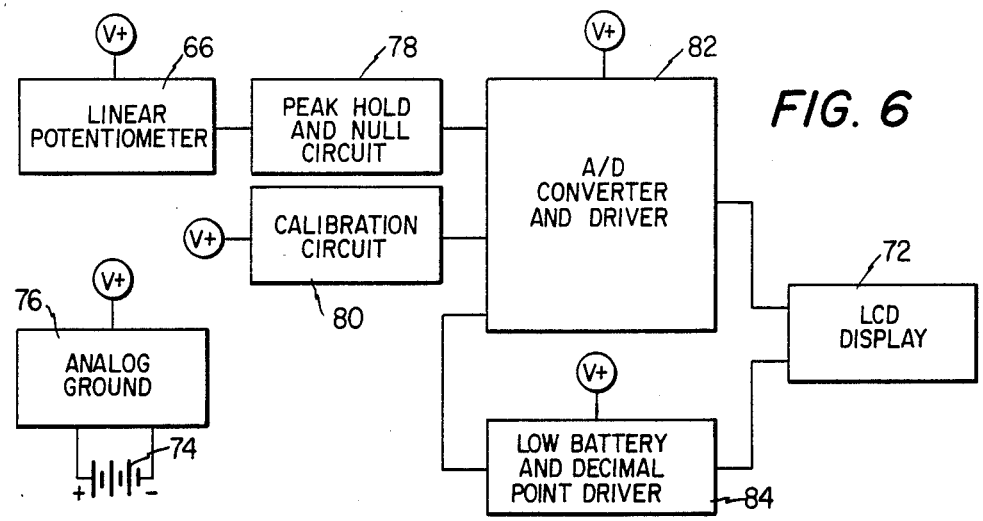
FIG. 6 is a block diagram of the electronic circuit employed in the testing device.

The transducer module 52 further includes an electronics package 70 mounted on the upper side of the reference arm 18. The electronics package 70 measures the change in resistance of the potentiometer 66 as forces are applied to the leg, representing the displacement of the tibia relative to the femur, and translates this resistance change to a displacement for display on LCD display 72. The functions of the electronic package 70 are best described with reference to FIG. 6, which illustrates a flow chart of the electronic components within the package 70. A power source is employed which is represented by battery 74 and an analog ground circuit 76 to establish the supply voltage V+. The analog ground circuit 76 establishes an analog ground that is precisely in the middle of the voltage between the two terminals of battery 74. This permits ratiometric output of the A/D converter. In other words, as the supply voltage decreases, the ratio of the input voltage to the reference voltage remains constant. A single operational amplifier can be used in an inverter configuration with the positive input voltage from battery 74 divided between two 10 Kohms resistors to form the analog ground circuit 76. The package 70 can use a standard 9 volt alkaline battery and maintain calibration even though the battery voltage may drop during use.

The V+ voltage is applied across the entire resistance of the potentiometer 66. The wiper within the potentiometer 66 therefore senses a voltage which varies as the input shaft 68 is rotated. The voltage signal from the wiper of the potentiometer 66 is transmitted to a peak hold and null circuit 78. The circuit 78 initially permits the operator to zero the device and display 72 prior to application of force with the device. The initial position of the inner tube 56 before application of a force will vary because the leg size of the patients tested will vary. It is therefore necessary to set a zero position for each patient prior to application of the force to evaluate the displacement when the force is applied.

As the force is applied, the circuit 78 detects the variation in voltage across the potentiometer 66 as the input shaft 68 is rotated. Because the force is limitd by the use of the torque limiter 26, the maximum displacement measured will correspond to the maximum force applied. Therefore, the circuit 78 has a holding circuit to retain the value of the peak displacement represented by the voltage across potentiometer 66. The peak hold and null circuit 78 can consist of an inverter, which presents a high impedance tothe input voltage from the wiper of potentiometer 66 so that loading effects are minimized. A low leakage diode can maintain the peak voltage by preventing leakage into the lower impedance output of an operational amplifier. A capacitor, for example of 10 microfarad capacity, can be used to charge to the peak value during force application and can be discharged after measurement to reset the circuit. Preferably, the reset and null functions are performed by a single switch on the package 70.

A calibration circuit 80 is provided to calibrate the device and can include a precision 10 Kohm potentiometer with the wiper voltage establishing a reference high voltage. The signal voltage and reference voltage are input to the A/D converter and driver 82. In one device constructed in accordance with the teaching of a present invention, the converter 82 was an Intersil ICL 7126. This Intersil chip provides an 11 bit A/D converter, a back plane driver and a 7 segment decoder for a 3.5 digit LCD display. External components are needed only to provide timing for a clock circuit and the integrator circuit. In the device constructed in accordance with the teachings of the present invention, the clock circuit was provided with a rate of 3 samples per second. The A/D converter and driver circuit 82 controls the output of the LCD display 72 to provide a direct read out of the displacement for the operator in the relevant measurement system, usually millimeters with an accuracy of 0.1 millimeter.

Since operation with a low battery voltage will cause operational amplifiers in the A/D converter to operate a nonlinear fashion, a low battery and decimal point driver circuit 84 is provided. The circuit 84 can operate to light a low battery indicator, preferably before the battery voltage drops below 6 volts. The low battery driver can consist of a comparator, with the positive voltage side maintained about 1.2 volts above the analog ground by means of two diodes in series. The input to the negative voltage side of the comparator is established by a voltage divider at ⅓ of the V+. When V+ drops to 3.6 volts above analog ground (i.e. when V+ divided by 3=1.2 volts), then the comparator output goes low, forcing a NAND gate input to the low battery indicator on the LCD display to go high and light the low battery indicator. A back plane drive on the A/D converter is used to maintain the high input to the NAND gate for the low battery indicator and the decimal point on the LCD display 72.

In one device constructed in accordance with the teachings of the present invention, a potentiometer 66 was employed with an output shaft 68 having a diameter of 3.18 millimeters and a circumference of 9.975 millimeters. The potentiometer was a 10 turn device which gives a total range for displacement of 99.75 millimeters. With slots 62 having a length of 3 inches with 1.5 inches between posts 58 and 60, a travel was permitted in the inner tube 56 of 1.25 inches, or 31.75 millimeters relative to the outer tube 54. This permits the potentiometer 66 to operate near the middle of its range, avoiding nonlinearities at the ends of the range.

If 4.5 volts was applied across the potentiometer 66, the full scale voltage for measurement by circuit 78 would be the total mechanical range of the potentiometer divided by the range of the device 10. Thus, the full scale voltage range would be equal to 31.75 millimeters divided by 99.75 millimeters×4.5 volts=1.432 volts. Since the A/D converter uses eleven bits, the converter error is 1.432 volts divided by 2048×2 or +/−0.35 millivolts. Thus, full scale erroe due to the converter is +/−0.024%. As V+ drops to 3.2 volts, the error remains constant. The potentiometer linearity is +/−0.25%. Thus the combined error is 0.274%, yielding a total of error +/−0.104 millimeters.

The knee ligament testing device 10 therefore provides a safe and effective way of measuring the condition of the ACL ligament. The device 10 provides a safety limit on the force that may be applied to the leg and also maintains this limit as a constant so that the device produces high reproducibility. The electronic measurement of the displacement and display thereof provides a highly accurate and convenient method for viewing the magnitude of the displacement.

Although one embodiment of the invention has been described in the foregoing Detailed Description and illustrated in the accompanying drawings, it will be understood that the invention is not limited to the embodiment disclosed, but is capable of numerous rearrangements, modifications and substitutions of parts and elements without departing from the spirit of the invention. Accordingly, the present invention is intended to encompass such rearrangements, modifications and substitutions of parts and elements as fall within the spirit and scope of the invention.

We claim:

1. An apparatus for measuring the relative displacement of the tibia and femur upon application of a force by operator, comprising:

a force application arm defining a rigid surface for contacting the lower leg for application of force on the tibia;
a reference arm pivotally hinged to said force application arm and defining a rigid surface for contacting the upper leg for application of a force on the femur to counter the force applied to the tibia through the force application arm;
means for limiting the force applied to the tibia to a predetermined maximum force to provide reproducibility of displacement measurement and to prevent application of excessive force;
a displacement sensor mounted on said reference armhaving an element mounted for movement relative to said reference arm along an axis generally parallel the direction of the displacement of the tibia relative to the femur, one end of the element positioned so as to contact the lower leg in a fixed relation with the tibia at the level of the tibial tubercle; and
means for measuring the displacement between the reference arm and the element when the force is applied, the displacement corresponding to the displacement between the femur and tibia.

2. The apparatus of claim 1 wherein said means for measuring comprises a rotary potentiometer and a means for converting linear motion of the element relative to the reference arm into rotary motion of the rotary potentiometer for measuring the displacement to an accuracy of approximately 0.1 millimeters.

3. The apparatus of claim 2 further comprising electronic circuitry means for measuring the electrical characteristics of the rotary potentiometer to generate an output signal to indicate the displacement, said electronci circuitry nulling the response to the potentiometer before application of the force and holding the peak value of the displacement after application of the force.

4. The apparatus of claim 2 wherein said potentiometer has an input shaft and said element has first and second posts extending therefrom and a string extending between said posts and wrapped about the input shaft of said potentiometer, linear movement of the element being transformed into a rotay motion of the input shaft of the potentiometer.

5. The apparatus of claim 4 wherein said reference arm defines a structure having at least one slot therein aligned with the direction of displacement, the first and second posts extending through the slot and confining the element to motion in a plane parallel to the sagittal plane through the midpoint of the knee.

6. The apparatus of claim 1 wherein said means for limiting the force supplied to the tibia includes a torque limiter.

7. An apparatus for measuring the relative displacement of the tibia and femur upon application of a force by an operator, comprising:

a force application arm defining a rigid surface for contacting the calf of the leg for application of a force on the tibia;
a reference arm pivotally hinged to said force application arm, the hinge being positioned below the ankle of the leg being tested when contacted by the surface of the force application arm, said reference arm defining a rigid surface for contacting the upper leg for application of the force on the femur to counter the force applied to the tibia through the force application arm, resulting in a displacement of the tibia relative to the femur;
a torque limiter having an input and an output, the force application arm having an aperture formed therein for receiving a portion of the output of the torque limiter, the input of the torque limiter accepting a wrench for application of a torque to the input, the torque limiter limiting the maximum torque at the output independent of the input so that a predetermiend maximum force can be applied through the force application arm to provide reproducibility of displacement measurement and prevent application of excessive force;

a movable member mounted on the reference arm for movement generally along the direction of the displacement of the tibia relative to the femur, one end of said member having a pad for contacting the lower leg at the level of the tibial tubercle, application of force on the lower leg through the force application arm resulting in a displacement of the tibia relative to the femur and a corresponding movement of the member relative to the reference arm, said member having first and second posts extending therefrom in a spaced apart relation, the reference arm having structure defining at least one slot generally aligned in the direction of displacement of the tibia relative to the femur, the first and second posts extending through the slot for guiding the member for motion in a plane parallel to the sagittal plane through the midpoint of the knee;

a rotary potentiometer mounted on said reference arm, said potentiometer having an input shaft extending between said first and second posts on the member, a strong being secured to said first post, extending to the input shaft of the potentiometer and wrapped thereabout and secured to the second post, motion of the member inducing rotation in the input shaft of the potentiometer; and means for measuring the variation in resistence of the potentiometer from a position before application of force to a position achieved with application of the predetermined maximum force to measure the displacement of the tibia relative to the femur.

8. The apparatus of claim 7 wherein said measuring means includes a voltage source for application across the potentiometer, the potentiometer having a wiper arm, the voltage at the wiper arm of the potentiometer varying as the potentiometer input shaft is rotated and means for measuring the change in voltage at the wiper arm prior to application of force and when the predetermined maximum force is applied, said measuring means further including a display means for displaying the displacement of the tibia relative to the femur and means for converting the charge in voltage to displacement to display the displacement on the display means.

9. The apparatus of claim 7 wherein said potentiometer is selected to provide an accuracy of approximately plus or minus 0.1 millimeters in measured displacement of the tibia relative to the femur.

10. An apparatus for measuring the displacement of the tibia relative to the femur upon application of a force by an operator for testing the ACL ligament in the knee, comprising:

a force application arm having a frame and a rigid surface on the top of the frame, the rigid surface for contacting the calf of a leg to be examined to apply a force on the tibia;

a reference arm pivotally hinged to said force application arm and comprising a frame, the hinge being located at a greater distance from the knee than the ankle of the patient, said reference arm including a support having a rigid surface at one end for contacting the upper leg at the patella, the opposite end of the support having a surface for application of a force on the patella to counter the force supplied to the tibia through the force application arm;

a torque limiter having an input and output, the output being limited to a predetermined maximum torque independent of the torque at the input, the frame of said force application armhaving an aperture for receiving the output of the limiter, application of a torque to the input at least equal to the predetermined maximum torque applying a force on the tibia through the force application arm limited to a predetermined maximum force to provide reproducibility of displacement measurement and to prevent application of excessive force to the leg of the patient;

an outer tube fixed relative to the reference arm and having an aperture generally aligned with the direction of displacement of the tibia relative to the femur and centered over the tibial tubercle when the leg of the patient is supported on the force application arm, said outer tube having at least one slot formed therethrough generally extending along the direction of displacement of the tibia and in a plane generally perpendicular to a plane parallel to the sagittal plane through the midpoint of the knee;

an inner tube extending into the aperture in said outer tube and confined for movement generally along the direction of displacement of the tibia by the outer tube; said inner tube having means at one end for contacting the lower leg at the level of the tibial tubercle so that the inner tube is movable with the lower leg, said inenr tube having a first and second post extending therefrom through the slot in the outer tube, said slot and posts confining the inner tube to motion within the plane parallel the sagital plane through the midpoint of the knee;

a multiturn linear potentiometer mounted on said reference arm adjacent the outer tube, said potentiometer having an input shaft extending between said first and second posts, said potentiometer further having a wiper arm;

a string extending between said first and second posts and wrapped about the input shaft of the potentiometer so that linear movement of the inner tube relative to the outer tube is translated into rotary motion of the input shaft of the potentiometer, the displacement of the tibia relative to the femur upon application of force to the tibia resulting in a corresponding rotation of the input shaft of the potentiometer;

a voltage source for applying a voltage across the entire resistance of the potentiometer, the input shaft moving the wiper arm, the voltage at the wiper arm therefore corresponding to the displacement of the tibia relative to the femur;

means for sensing the voltage at the wiper arm of the potentiometer prior to application of force and at the time of application of the predetermined maximum force and converting the difference in voltage to the displacement; and display means displaying the displacement measured by the means for sensing.

* * * * *

UNITED STATES PATENT AND TRADEMARK OFFICE
CERTIFICATE OF CORRECTION

PATENT NO. : 4,583,554                               Page 1 of 2

DATED : APRIL 22, 1986

INVENTOR(S) : JONATHAN S. MITTELMAN and JOHN S. ROMINE

It is certified that error appears in the above-identified patent and that said Letters Patent is hereby corrected as shown below:

Column 2, line 8, delete "displcement" and insert
    --displacement--;

Column 2, line 23, delete "muxcular" and insert --muscular--;

Column 2, line 34, delete "Alcottstreet" and insert
    --Alcott Street--;

Column 2, line 38, delete "ahigh" and insert --a high--;

Column 2, line 45, delete "thetibia" and insert --the tibia--;

Column 2, line 49, delete "armis" and insert --arm is--;

Column 3, line 14, delete "applicationof" and insert
    --application of--;

Column 3, line 24, delete "techings" and insert --teachings--;

Column 4, line 26, delete "poratin" and insert --poration--;

Column 4, line 29, delete "potion" and insert --portion--;

Column 4, line 33, delete "section";

Column 4, line 38, delete "frictinal" and insert --frictional--;

Column 4, line 51, delete "predetermiend" and insert
    --predetermined--;

Column 5, line 3, delete "displacementof" and insert
    --displacement of--;

Column 5, line 10, delete "thatof" and insert --that of--;

Column 5, line 27, delete "thehand" and insert --the hand--;

Column 5, line 60, delete "displacementof" and insert
    --displacement of--;

UNITED STATES PATENT AND TRADEMARK OFFICE
CERTIFICATE OF CORRECTION

PATENT NO. : 4,583,554
DATED : APRIL 22, 1986
INVENTOR(S) : JONATHAN S. MITTELMAN and JOHN S. ROMINE It is certified that error appears in the above-identified patent and that said Letters Patent is hereby corrected as shown below:

```
Column 6, line 28, delete "limitd" and insert --limited--;
Column 6, line 35, delete "tothe" and insert --to the--;
Column 7, line 11, delete "drive" and insert --driver--;
Column 7, line 35, delete "erroe" and insert --error--;
Column 8, line 9, delete "armhaving" and insert --arm having--;
Column 8, line 30, delete "electronci" and insert --electronic--;
Column 8, line 38, delete "rotay" and insert --rotary--;
Column 9, line 3, delete "predetermiend" and insert
     --predetermined--;
Column 9, line 27, delete "strong" and insert --string--;
Column 10, line 8, delete "armhaving" and insert --arm having--;
Column 10, line 31, delete "tube;" and insert --tube,--;
Column 10, line 34, delete "inener" and insert --inner--;
Column 10, line 37, delete "sagital" and insert --sagittal--.
```

Signed and Sealed this

Thirtieth Day of September 1986

[SEAL]

Attest:

DONALD J. QUIGG

Attesting Officer     Commissioner of Patents and Trademarks